(12) United States Patent
Friedrich et al.

(10) Patent No.: US 11,767,396 B2
(45) Date of Patent: Sep. 26, 2023

(54) FLUORINE COMPOUNDS

(71) Applicant: Merck Patent GmbH, Darmstadt (DE)

(72) Inventors: Reiner Friedrich, Seeheim-Jugenheim (DE); Fabian Koch, Pfungstadt (DE)

(73) Assignee: Merck Patent GmbH, Darmstadt (DE)

( * ) Notice: Subject to any disclaimer, the term of this patent is extended or adjusted under 35 U.S.C. 154(b) by 62 days.

(21) Appl. No.: 17/357,193

(22) Filed: Jun. 24, 2021

(65) Prior Publication Data

US 2021/0317259 A1 Oct. 14, 2021

Related U.S. Application Data

(62) Division of application No. 16/650,489, filed as application No. PCT/EP2018/075730 on Sep. 24, 2018, now Pat. No. 11,174,339.

(30) Foreign Application Priority Data

Sep. 26, 2017 (EP) .................................... 17193042

(51) Int. Cl.
*C08G 59/02* (2006.01)
*C07D 303/24* (2006.01)
*C09D 163/08* (2006.01)

(52) U.S. Cl.
CPC ......... *C08G 59/027* (2013.01); *C07D 303/24* (2013.01); *C09D 163/08* (2013.01)

(58) Field of Classification Search
CPC .................................................... C07D 163/00
See application file for complete search history.

(56) References Cited

U.S. PATENT DOCUMENTS

| | | | |
|---|---|---|---|
| 10,464,874 B2 | 11/2019 | Friedrich et al. | |
| 10,689,522 B2 | 6/2020 | Friedrich | |
| 11,174,339 B2 * | 11/2021 | Friedrich | C07D 303/24 |
| 2017/0349760 A1 | 12/2017 | Friedrich | |
| 2019/0322776 A1 | 10/2019 | Fang et al. | |
| 2020/0277247 A1 | 9/2020 | Friedrich | |

FOREIGN PATENT DOCUMENTS

| | | |
|---|---|---|
| WO | 15124290 A1 | 8/2015 |
| WO | 16096128 A1 | 6/2016 |
| WO | 16096129 A1 | 6/2016 |
| WO | 17216201 A1 | 12/2017 |

OTHER PUBLICATIONS

American Chemical Society. Chemical Abstract Service. RN 54208-65-0. Entered into STN/date first made available to public: Nov. 16, 1984. (Year: 1984).*
Solov'ev, D. V.; Kolomenskaya, L. V.; Rodin, A. A.; Zenkevich, I. G.; Lavrent'ev, A. N.: "Fluorine-containing glycidyl ethers. Synthesis and spectra", Zhurnal Obshchei Khimii, vol. 61, No. 3, Jan. 1, 1991 (Jan. 1, 1991), pp. 673-679, XP009509482, ISSN: 0044-460X.
J.D. LaZerte, R.J. Koshar, "The Free Radical Catalyzed Addition . . . "Journal of the American Chemical Society, 1955, 77, pp. 910-914.
International Search Report PCT/EP2018/075730 dated Nov. 29, 2018 (pp. 1-2).
American Chemical Society. Chemical Abstract Service. RN 122502-53-8. First date of public availability/entered into STN on Sep. 1, 1989. (Year: 1989).

* cited by examiner

*Primary Examiner* — John S Kenyon
(74) *Attorney, Agent, or Firm* — MILLEN, WHITE, ZELANO & BRANIGAN, PC; Ryan Pool

(57) ABSTRACT

The present invention relates to fluorine compounds (I), (II) and (III), to processes for the preparation thereof, and to the use thereof.

6 Claims, No Drawings

FLUORINE COMPOUNDS

The present invention relates to fluorine compounds, to processes for the preparation thereof, and to the use thereof.

Fluorinated compounds have long been a constituent in polymers for dirt-repellent coatings. Classical fluorine compounds are built up from longchain, perfluorinated alkyl chains (C6-C8) and are regarded as potentially bioaccumulative and toxic. The persistence and the associated environmental hazard of conventional C6 compounds are problematic. Fluorine-containing compounds are also used as interface promoters or emulsifier or viscosity reducer in paints, coatings or adhesives.

Efforts to date were aimed at investigating compounds which are shortchain and have a nominal breaking point, thereby intending to ensure the most complete decomposition (mineralisation) possible of the fluorinated units. Shorter-chain fluorine building blocks are more favourable from their ecotoxicological profiles, but often exhibit poorer properties in their areas of application.

Fluorine building blocks with the shortest possible chains are on the one hand helpful if the aim is to emit non-persistent compounds into the environment. On the other hand, the fluorine content is crucial for dirt repulsion. The less fluorine in the molecule, the poorer the effect. It would therefore be desirable to synthesise functionalisable macromolecules having a plurality of recurring units from shortchain fluorine-containing molecules (monomers). There is therefore a need for novel fluorine-containing compounds and for processes for the preparation of these compounds.

The present invention relates to compounds of the formulae (I), (II) and (III), to processes for the preparation thereof, to the use of these compounds for the preparation of further fluorinated compounds, to fluorinated compounds of the formulae (XI) to (XVI), and to the uses thereof.

The invention relates firstly to compounds of the formulae (I), (II) and (III):

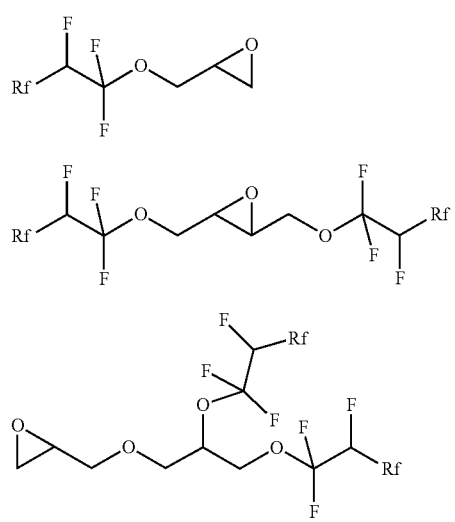

where

Rf is a fluorinated, linear or branched alkyl group, optionally containing further heteroatoms.

Rf is preferably a group of the formula $CF_3-(CF_2)_a-O_b-(CF_2)_c-O_d-$, where a=0, 1, 2 or 3, b=0 or 1, c=0, 1, 2 or 3 and d=0 or 1.

Rf is preferably a group of the formula $CF_3-(CF_2)_{0-3}-$ or of the formula $CF_3-(CF_2)_{0-3}-O-$.

The invention furthermore relates to a for the preparation of compounds of the formula (I) by reaction of compounds of the formula (IV) with glycidol (V) to give compounds of the formula (I)

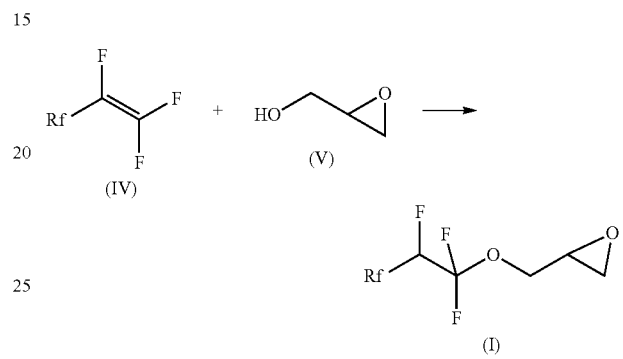

To this end, the corresponding perfluoroolefin is brought to reaction with a base, preferably in an alkali-metal carbonate or hydroxide, in an organic solvent, preferably an ether, such as dioxane, THF, but also acetonitrile, in a pressure reactor at elevated temperature, preferably 80-120° C., for several hours, preferably 6-16 hours. The epoxide is obtained here in good yield (70-95%)

The invention furthermore relates to a process for the preparation of compounds of the formula (II) by reaction of compounds of the formula (IV) with compounds of the formula (VI) to give compounds of the formula (II)

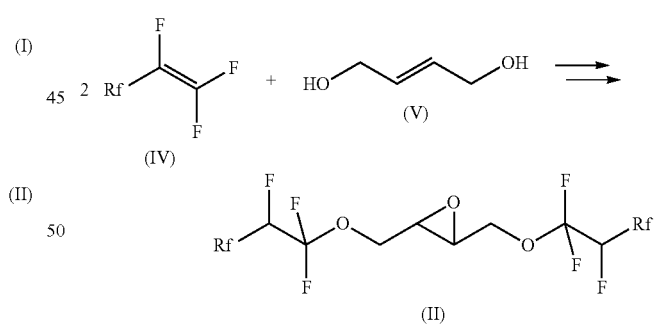

The invention furthermore relates to a process for the preparation of compounds of the formula (III) by reaction of compounds of the formula (IV) with compounds of the formula (VII) to give compounds of the formula (II)

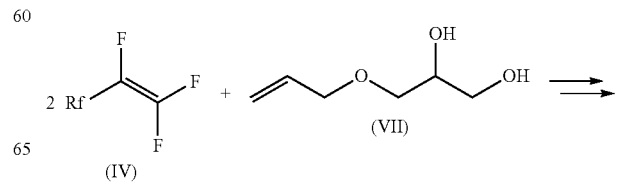

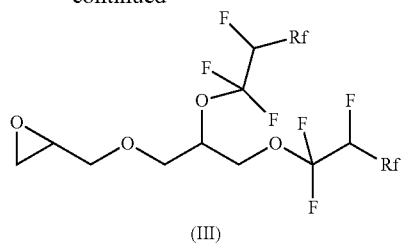

(III)

The group Rf has the meaning indicated for compounds (I), (II) and (III), in particular also the preferred meaning.

It has also proven successful in, the reaction of the perfluoroolefins with the above-mentioned dihydroxyalkylolefins, to carry out the reaction with a base, preferably an alkali-metal carbonate or hydroxide as base, in an organic solvent, preferably an ether, such as dioxane, THF, or also acetonitrile, in a pressure reactor at elevated temperature, preferably 80-120° C., for several hours (preferably 6-16 hours) in order to obtain the product in good yield (70-95%). The double bond is subsequently reacted here under known epoxidation conditions to give the corresponding monomer. The reaction with m-chloroperbenzoic acid or the Jacobsen epoxidation has proven successful particularly successful here.

The present invention now enables corresponding macromolecules of the formulae (VIII) to (X) to be prepared starting from the compounds of the formulae (I), (II) and (III) by polymerisation by known methods:

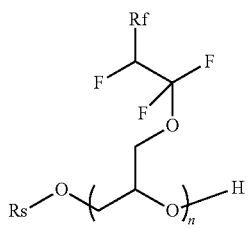

(VIII)

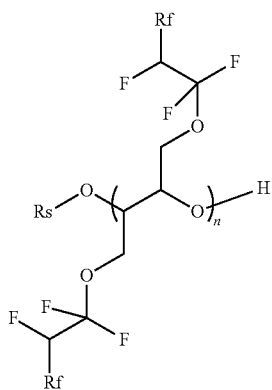

(IX)

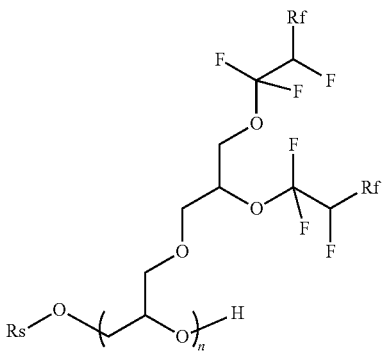

(X)

where

Rf is a fluorinated, linear or branched alkyl group, optionally containing further heteroatoms. The group Rf also has, in particular, the preferred meaning indicated for compounds (I), (II) and (III). Rs here is the optionally fluorinated alkyl group of a "starter" alcohol, which may likewise be fluorinated.

Rs preferably has the following structure:

Rs: Rf'—CHF—$CF_2$—$CH_2$—

The synthesis of the alcohols is described, for example, in J. D. LaZerte, R. J. Koshar Journal of the American Chemical Society 1955 77 910-914.

Rf' is preferably a group of the formula $CF_3$—$(CF_2)_a$—$O_b$—$(CF_2)_c$—$O_d$—, where a=0, 1, 2 or 3, b=0 or 1, c=0, 1, 2 or 3 and d=0 or 1.

Rf' is particularly preferably a group of the formula $CF_3$—$(CF_2)_{0-3}$— or of the formula $CF_3$—$(CF_2)_{0-3}$—O—.

These "comb" polymers of the formulae (VIII) to (X) each have a terminal of each group which can be reacted further. For dirt-repellent coatings, it is advantageous to esterify the (meth)acryloyl group. These monomers of the formulae (XI), (XIII) and (XV) can then in turn be converted into polymers which are matched to the precise requirements of the textile fibre.

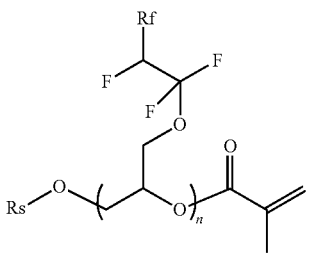

(XI)

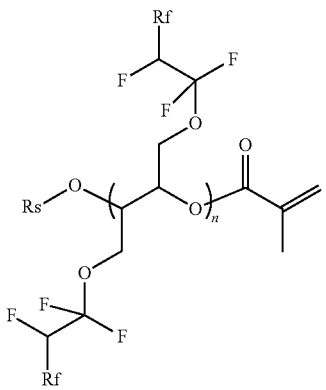

(XIII)

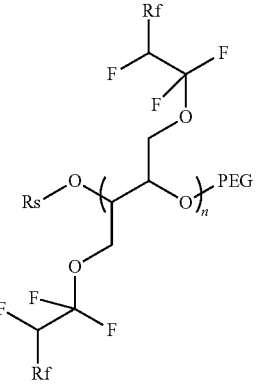

(XIV)

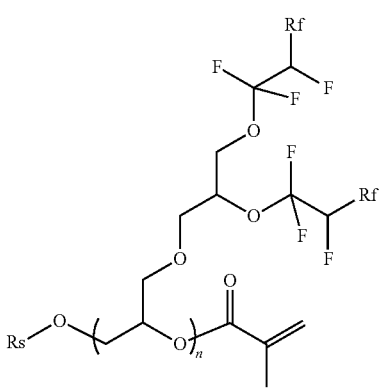

(XV)

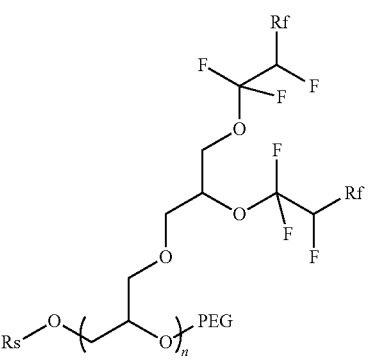

(XVI)

where

Rf is a fluorinated, linear or branched alkyl group, optionally containing further heteroatoms. The group Rf also has, in particular, the preferred meaning indicated for compounds (1), (II) and (III). The group Rs has the meaning indicated for the compounds of the formulae (VIII)-(X), in particular also the preferred meaning.

The conversion to the (meth)acrylates is advantageously carried out here starting from the acid chlorides or anhydrides by methods known to the person skilled in the art.

In addition, ethylene oxide can also furthermore be adducted onto the terminal OH group of the "comb" polymers of the formulae (VIII) to (X). Thus, non-ionic surfactants of the formulae (XII), (XIV) and (XVI) containing fluorinated psych groups are obtained.

(XII)

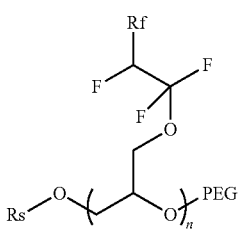

where

Rf is a fluorinated, linear or branched alkyl group, optionally containing further heteroatoms. The group Rf also has, in particular, the preferred meaning indicated for compounds (I), (II) and (III). The group Rs has the meaning indicated for the compounds of the formulae (VIII)-(X), in particular also the preferred meaning.

It is advantageous in the case of compounds XII, XIV and XVI that, for their preparation, the further reaction of the "comb" polymers of the formulae (VIII) to (X) with ethylene oxide to give the non-ionic surfactant can be carried out in a batch, since the reaction conditions (catalyst and temperature) are identical with the polymerisation of the fluorinated epoxides.

The compounds according to the invention can preferably have a particular surface activity. The compounds according to the invention, in particular the preferred compounds, may in addition have improved environmental properties, since they do not degrade chemically or biologically to give longchain PFCAs or PFASs. The compounds according to the invention can preferably be converted completely into mineralisable/regeneratable compounds by corresponding environmental influences.

The invention likewise relates to the use of compounds of the formulae (VIII) to (XVI) and compositions comprising these compounds.

The compounds according to the invention can be used alone or as a mixture, also with other fluorinated and/or unfluorinated compounds, in particular for the preparation of functional coatings and surface modifications of all types on articles both for the indoor and outdoor areas. In principle, all surfaces can be coated, in particular glass, ceramic, enamel, metals, plastics, elastomers, natural products, textiles, optionally after suitable pretreatment.

Besides the compounds of the invention, the coatings may also comprise solvents, additives, surfactants, assistants and fillers. Mention may also be made by way of example of silicone particles and optionally surface-modified pigments.

Preferred areas of use are, for example, the use of the compounds according to the invention in coatings for optical elements or textiles, such as, for example, the use in anti-fingerprint coatings, for example for displays, optical lenses, spectacle lenses, lenses for cameras, binoculars, window panes or mirrors, or as hydrophobicising agents for textile finishing.

The compounds according to the invention or mixtures comprising them can be applied to a suitable surface, over the full area or a part-area, by various coating processes known to the person skilled in the art, for example by means of CVD, PVD, spray-coating, ink-jet, offset processes.

The invention also relates to compositions which comprise at least one of the compounds according to the invention, where the compositions may also comprise solvents, additives, surfactants, assistants and fillers.

The invention also relates to coated articles, in particular the above-mentioned articles, whose coating has been produced using at least one compound according to the invention. Preference is given to displays, optical lenses, spectacle lenses, lenses for cameras, binoculars, window panes, mirrors and textiles.

The compounds of the formulae (VIII) to (X) and (XII), (XIV) and (XVI) can preferably be used as surface-active agents, preferably as surfactant, hydrophobicising agent, interface promoter, viscosity reducer, foam stabiliser or emulsifier. The present invention therefore furthermore relates to the use of the compounds according to the invention and the preferred embodiments described above as surface-active agents, for example for improving the flow behaviour and the wetting capacity of coating formulations in particular of the said particularly preferred compounds.

Besides these compounds, the mixtures according to the invention may also comprise solvents, additives, assistants and fillers as well as unfluorinated surfactants. Mention may be made by way of example of silicone particles, plasticisers and surface-modified pigments.

Preferred areas of use are, for example, the use of the fluorosurfactants according to the invention as additives in preparations for surface coating, such as paints, coatings, protective paints, special coatings in electronic or semiconductor applications (for example photoresists, top antireflective coatings, bottom antireflective coatings) or in optical applications (for example photographic coatings, coatings of optical elements), in agrochemicals, in polishes and waxes, for example for furniture, flooring and automobiles, in particular in floor polishes, in fire-extinguishing compositions, lubricants, in photolithographic processes, in particular in immersion photolithography processes, for example in developer solutions, rinse solutions, immersion oils and/or in the photoresists themselves, especially for the production of printed circuits or in additive preparations for addition to corresponding preparations.

In addition, the compounds which can be used in accordance with the invention as surfactant are suitable for washing and cleaning applications, and for use as additives/surfactants in cosmetic products, such as, for example, hair- and body-care products (for example shampoos, hair rinses and hair conditioners), foam baths, creams or lotions having one or more of the following functions: emulsifiers, wetting agents, foaming agents, glidants, antistatic, agents for increasing the resistance to skin greases.

For use, the fluorosurfactants according to the invention are usually introduced into correspondingly designed preparations. Usual use concentrations are 0.01-1.0% by weight of the surfactants according to the invention, based on the preparation as a whole.

The present invention likewise relates to corresponding compositions comprising the fluorine compounds according to the invention. Such compositions preferably comprise a vehicle which is suitable for the respective application, and optionally further active substances and/or optionally assistants. Preferred compositions are paint and coating preparations, fire-extinguishing compositions, lubricants, washing and cleaning compositions and de-icers or developer solutions, rinse solutions, immersion oils and photoresists for photolithographic processes, in particular for immersion photolithography processes and in particular for the production of printed circuits, agrochemicals, floor polishes, cosmetic products or hydrophobicising compositions for textile finishing or glass treatment. Preferred compositions here are paint and coating preparations and printing inks.

In addition, the present invention also relates to water-based coating formulations which comprise the fluorosurfactants according to the invention, alone or in a mixture with additives. Coating formulations based on the following synthetic film formers are preferably used: polycondensation resins, such as alkyd resins, saturated/unsaturated polyesters, polyamides/imides, silicone resins; phenolic resins; urea resins and melamine resins, polyaddition resins, such as polyurethanes and epoxy resins, polymerisation resins, such as polyolefins, polyvinyl compounds and polyacrylates.

In addition, the fluorosurfactants according to the invention are also suitable for use in coatings based on natural products and modified natural products. Preference is given to coatings based on oils, polysaccharides, such as starch and cellulose, and also based on natural resins, such as cyclic oligoterpenes, polyterpenes and/or shellac.

The fluorosurfactants according to the invention can be used both in physically curing (thermoplastics) and also in crosslinking (elastomers and thermosets) aqueous coating systems. The fluorosurfactants according to the invention preferably improve the flow and wetting properties of the coating systems.

The present invention relates to all uses mentioned here of fluorosurfactants to be employed in accordance with the invention, in particular of the preferred compounds. The respective use of fluorosurfactants for the said purposes is known to the person skilled in the art, meaning that the use of the fluorosurfactants to be employed in accordance with the invention presents no problems.

The following examples explain the present invention in greater detail without restricting the scope of protection.

EXAMPLES

The NMR spectra are measured using a Bruker 400 MHz spectrometer with internal standard.

The IR spectra are measured using a Bruker Alpha Platinum-ATR spectrometer.

Determination of the Static Surface Tension The static surface tensions γ of aqueous surfactant solutions having various concentrations c (grams per litre) are determined.

Instrument: Dataphysics tensiometer (model DCAT 11) Temperature of the measurement solutions: 20°±0.2° C.

Measurement method employed: measurement of the surface tension using the Wilhelmy plate method in accordance with DIN EN 14370.

Plate: platinum, length=19.9 mm In the plate method, the surface or interfacial tension of the surfactant solution is calculated from the force acting on the wetted length of a plate, in accordance with the following formula:

$$\gamma = \frac{F}{L \cdot \cos\theta} = \frac{F}{L}$$

γ=interfacial or surface tension; F=force acting on the balance; L=wetted length (19.9 mm); θ=contact angle. The plate consists of roughened platinum and is thus optimally wetted so that the contact angle θ is close to 0°. The term cos θ therefore reaches approximately the value 1, so that only the measured force and the length of the plate have to be taken into account.

Abbreviations
EO ethylene oxide units
THF tetrahydrofuran
MTBE tert-butyl methyl ether
PPVE perfluoropropyl vinyl ether
b.p. boiling point
wt % percent by weight

Example 1

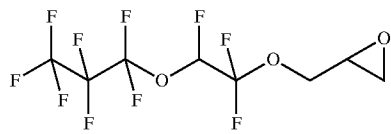 [SMILES: FC(OC(F)(F)C(F)(F)C(F)(F)F)C(F)(F)OCC1CO1]

21.78 g of glycidol, 93.86 g of PPVE, 12.19 g of potassium carbonate; 130 ml of dioxane The starting materials are combined in a 300 ml pressure reactor and stirred at 110 C for 24 h. At the beginning of the reaction, a pressure of 4.5 bar becomes established, this drops to 0.5 bar overnight. Water and MTBE are added to the reaction mixture, and the phases are separated. The aqueous phase is extracted with 2×30 ml of MTBE and the combined organic phase is washed with 40 ml of water and 40 ml of saturated NaCl solution. The extract is dried over sodium sulfate and the solvent is distilled off. Product weight: 90.87 g The product was distilled in vacuo.

| $T_{bath}$ °C. | $T_{head}$ °C. | p mbar |
|---|---|---|
| 50.3 | 24.1 | 0.80 |

Example 2

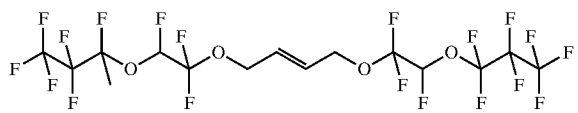 [SMILES: CC(F)(OC(F)C(F)(F)OC/C=C/COC(F)(F)C(F)OC(F)(F)C(F)(F)C(F)(F)F)C(F)(F)C(F)(F)F]

10.5 g of 1,4-butenediol and 80.0 g of PPVE 2.01 g of KOH and 40 g of acetonitrile are combined in a pressure reactor and the mixture is heated to 80° C. After 16 hours, the reaction is complete. Water and MTBE are added to the reaction mixture and the phases are separated. The aqueous phase is extracted with 2×30 ml of MTBE. The combined organic phase is washed with 50 ml of water and 50 ml of saturated NaCl solution. The extract is dried over sodium sulfate. The solvent is removed in vacuo. Yield: m=56.26 g
$^1$H-NMR: 7.2 ppm (dt, 2H, —CFH); 5.9 ppm (t, 1.5H, —CH=CH—); 5.7 ppm (t, 0.5H, —CH=CH—) 4.6 ppm (d, 1H, —CH$_2$—O); 4.5 ppm (d, 3H, —CH$_2$—O); 1H-NMR: 7.2 ppm (d, 1H, —CH$_2$—O); 4.5 ppm (d, 3H, —CH$_2$—O);

Example 3

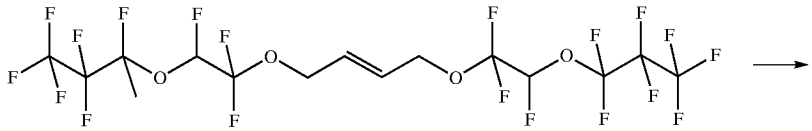

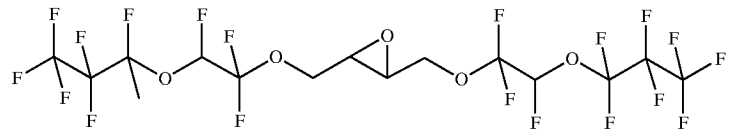

10 g of the olefin from Example 2 is initially introduced in 40 ml of acetonitrile in a three-necked flask under protective-gas atmosphere. 7 g of m-chloroperbenzoic acid is subsequently added with cooling and the reaction mixture is stirred at 80° C. for 20 hours. Water and MTBE are added to the reaction mixture and the phases are separated. The aqueous phase is extracted with 2×30 ml of MTBE. The combined organic phase is then washed with in each case 40 ml of water and 40 ml of saturated NaCl solution. The extract is subsequently dried over sodium sulfate and the solvent is distilled off. A white solid remains as residue. Product weight: 15.22 g

Example 4
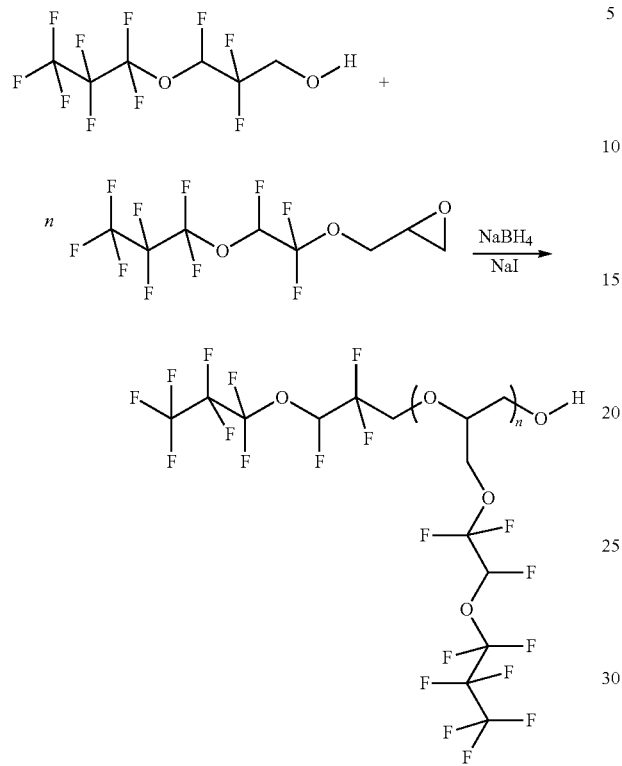
The epoxide prepared in Example 1 is reacted with NaBH$_4$ and NaI complex as initiator at 120° C. in a steel autoclave to give the corresponding PEG. The molecular weight can be adjusted via the amount of initiator and the reaction time/temperature.
The invention claimed is:
1. A compound of the formulae (XI) to (XVI)
(XI)
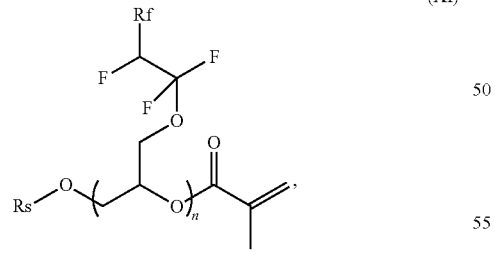
(XII)
(XIII)
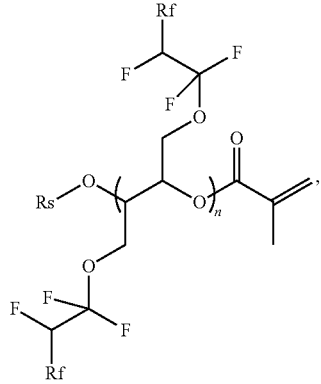
(XIV)
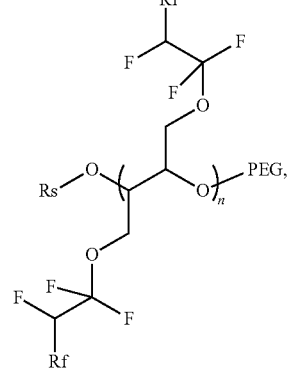
(XV)
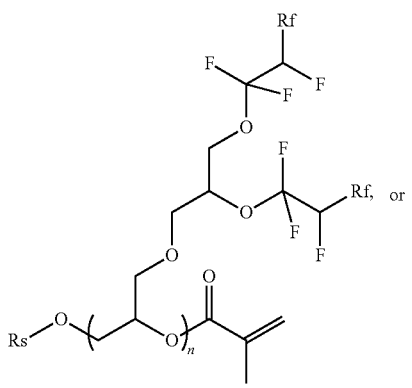
or
(XVI)
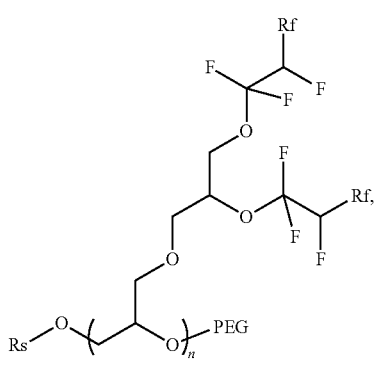

where
Rs is an optionally fluorinated alkyl group,
n is a number of from 5 to 20,
PEG is a polyethylene oxide group and
Rf is a group of the formula $CF_3-(CF_2)_a-O_b-(CF_2)_c-O_d-$,
where
a=1, 2 or 3,
b=0 or 1,
c=0, 1, 2 or 3 and
d=0 or 1.

2. The compound of claim 1, wherein Rf is a group of the formula $CF_3-(CF_2)_{1-3}-$ or $CF_3-(CF_2)_{1-3}-O-$.

3. An additive in a composition, wherein the composition is selected from the group consisting of: paints, coatings, printing inks, protective coatings, special coatings in electronic or optical applications, photoresists, top antireflective coatings or bottom antireflective coatings, developer solutions and wash solutions and photoresists for photolithographic processes, cosmetic products, agrochemicals, floor polishes, photographic coatings and coatings of optical elements; and the additive comprises a compound of claim 1.

4. A composition comprising one or more compounds according to claim 1 and a vehicle which is suitable for the respective application and optionally further specific active substances.

5. The composition according to claim 4, characterised in that the composition is selected from the group consisting of: paint and coating preparations, fire-extinguishing compositions, lubricants, washing and cleaning compositions, de-icers, developer solutions and wash solutions and photoresists for photolithographic processes, cosmetic products, agrochemicals, floor polishes and hydrophobicising compositions for textile finishing or glass treatment.

6. A coated article whose coating has been produced using at least one compound according to claim 1.

* * * * *